United States Patent [19]

Labat et al.

[11] Patent Number: 6,011,173
[45] Date of Patent: Jan. 4, 2000

[54] STABILIZATION OF THIOACETIC ACID

[75] Inventors: Yves Labat, Le Bouscat; Bernard Monguillon, Salies de Bearn, both of France

[73] Assignee: Elf Acquitaine Exploration Production, France

[21] Appl. No.: 09/172,173

[22] Filed: Oct. 14, 1998

[30] Foreign Application Priority Data

Oct. 15, 1997 [FR] France .................................. 97-12898

[51] Int. Cl.$^7$ .................................................. C07C 327/06
[52] U.S. Cl. .............................................. 562/26; 252/407

[58] Field of Search .................................................. 562/26

[56] References Cited

FOREIGN PATENT DOCUMENTS 1417154   7/1964   France .
60-142953 7/1985   Japan .

*Primary Examiner*—Michael G. Ambrose
*Attorney, Agent, or Firm*—Bell, Boyd & Lloyd

[57] ABSTRACT

To avoid the degradation of thioacetic acid on storage, from 0.005 to 0.5% of a chloroacetic acid, preferably dichloroacetic acid, is added thereto.

10 Claims, No Drawings

STABILIZATION OF THIOACETIC ACID

FIELD OF THE INVENTION

The present invention concerns the field of thiocarboxylic acids and relates more particularly to the stabilization of thioacetic acid.

BACKGROUND OF THE INVENTION

This acid of formula $CH_3$—COSH, manufactured by reaction of hydrogen sulphide with acetic anhydride (patent FR 1,417,154), is currently used as an intermediate for synthetizing pharmaceutical products such as captopryl (antihypertensive agent).

It is known that thioacetic acid has a tendency, on hydrolysis, to form various sulphur-containing or oxygen-containing compounds which lower the thioacetic acid assay of the commercial product. This instability of thioacetic acid is due in particular to the formation of hydrogen sulphide and acetic acid according to the reaction:

catalysed by acidic species (Tetrahedron, 1965, vol. 21, pp. 835). Diacetyl sulphide ($CH_3CO$—S—$COCH_3$) and diacetyl disulphide ($CH_3CO$—S—S—$COCH_3$) are also formed.

In order to stabilize thioacetic acid, patent JP 1,345,605 has proposed adding a phosphorus-containing inorganic acid or a strong organic acid (pKa<3.3) thereto. Apart from oxalic acid, the other compounds mentioned (phosphorous acid, citric acid, methanesulphonic acid) do not have a sufficient stabilizing action for good conservation of thioacetic acid on storage.

DESCRIPTION OF THE INVENTION

It has now been found, surprisingly, that chloroacetic acids allow thioacetic acid to be stabilized satisfactorily at 50° C., and do so for a period of 1 to 2 months which is necessary for transportation of this product over long distances.

It has also been observed that, in the chloroacetic acid series comprising monochloroacetic acid (pKa=2.9), dichloroacetic acid (pKa=1.3) and trichloroacetic acid (pKa=0.7), dichloroacetic acid has the most effective stabilizing action.

A first subject of the invention is thus a process for stabilizing thioacetic acid, characterized in that a sufficient amount of a chloroacetic acid, preferably dichloroacetic acid, is added thereto.

The subject of the invention is also a composition consisting essentially of thioacetic acid and of a small amount of a chloroacetic acid, preferably dichloroacetic acid.

The amount of stabilizing chloroacetic acid can range from 50 to 5000 ppm, but is preferably between 100 and 2000 ppm (0.01 to 0.2% by weight).

In order to obtain the optimum stabilizing action, it is advantageous to add the stabilizing chloroacetic acid to a freshly distilled thioacetic acid which contains as little water as possible (water<0.5%). Moreover, in order to avoid an atmospheric oxidizing action, it is desirable to isolate the stored product under nitrogen.

EXAMPLES

The examples which follow illustrate the invention without limiting it.

EXAMPLE 1 comparative

Freshly distilled thioacetic acid (purity=99.27%) was introduced into several glass vials which were sealed and kept in an oven at 50° C.

The vials were periodically cooled and opened in order to measure the thioacetic acid assay by gas chromatography. The results given in the following table show that after storage for 100 days, the purity of the product has fallen to 63%.

EXAMPLE 2 comparative

The process was performed as in Example 1, but adding 3000 ppm of oxalic acid to the thioacetic acid. After storage for 100 days, the loss of purity is about 10%.

EXAMPLES 3 and 4

The process was performed as in Example 1, but adding 3000 ppm of dichloroacetic acid (Example 3), or only 1000 ppm of this same acid (Example 4) to the thioacetic acid.

The results in the following table show that dichloroacetic acid is much more effective than oxalic acid since, after storage for 100 days, the thioacetic acid assay has fallen by only 2–3%, even with a dose times as low (Example 4).

| DURATION OF STORAGE | PURITY (%) OF THE THIOACETIC ACID | | | |
|---|---|---|---|---|
| At 50° C. (days) | Comparative Example 1 | Comparative Example 2 | Example 3 | Example 4 |
| 0 | 99.27 | 99.27 | 99.27 | 99.27 |
| 20 | 93.60 | 98.80 | 98.85 | 99.0 |
| 50 | 91.80 | 97.80 | 98.50 | 98.96 |
| 80 | 80 | 94.20 | 97.10 | 98.40 |
| 100 | 63 | 88.90 | 96.40 | 96.80 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for stabilizing thioacetic acid, comprising adding an effective amount of a chloroacetic acid thereto.

2. Process according to claim 1, wherein the stabilizer is dichloroacetic acid.

3. Process according to claim 1, wherein the amount of stabilizer ranges from 50 to 5000 ppm.

4. Process according to claim 3, wherein the amount is between 100 and 2000 ppm.

5. Process according to claim 1, wherein the stabilizer is added to a freshly distilled thioacetic acid.

6. Process according to claim 5, wherein the water content of the acid is less than 0.5%.

7. Process according to claim 1, wherein the stabilized product is stored in the absence of air.

8. Composition consisting essentially of thioacetic acid with 50 to 5000 ppm of a chloroacetic acid.

9. Composition according to claim 8, wherein the composition contains 100 to 2000 ppm of chloroacetic acid.

10. Composition according to claim 8, wherein the chloroacetic acid is dichloroacetic acid.

* * * * *